United States Patent [19]

Taylor

[11] Patent Number: 4,625,558
[45] Date of Patent: Dec. 2, 1986

[54] FUEL MONITORING SYSTEMS

[75] Inventor: Peter J. Taylor, Fareham, England

[73] Assignee: Plessey Overseas Limited, Ilford, England

[21] Appl. No.: 721,417

[22] Filed: Apr. 9, 1985

[30] Foreign Application Priority Data

Apr. 13, 1984 [GB] United Kingdom ............... 8409650

[51] Int. Cl.⁴ .................................. G01N 7/00
[52] U.S. Cl. ...................................... 73/64.2
[58] Field of Search .......................... 73/64.2, 19

[56] References Cited

U.S. PATENT DOCUMENTS 3,229,504  1/1966  Smith ......................... 73/64.2
3,738,154  6/1973  Henry ......................... 73/19
4,150,560  4/1979  Wieland ....................... 73/19

FOREIGN PATENT DOCUMENTS 1154078  4/1958  France ........................ 73/64.2
 830548  3/1960  United Kingdom .............. 73/64.2

Primary Examiner—Stewart J. Levy
Assistant Examiner—Hezron E. Williams
Attorney, Agent, or Firm—Fleit, Jacobson, Cohn & Price

[57] ABSTRACT

A fuel monitoring system comprises a centrifugal air separation chamber having input and output Venturi devices. The system is arranged so that fuel from the fuel tank of the aircraft is pumped to the input Venturi device which due to the pressure drop therein, serves to release air from the fuel before it passes into the centrifugal air separation chamber where the air released from the fuel is separated out and exhausted from the chamber, whereas the substantially de-aerated fuel passes from the separation chamber into the output Venturi device, which produces a pressure drop enabling the vapor pressure of the de-aerated fuel to be determined therefrom.

3 Claims, 5 Drawing Figures

FUEL MONITORING SYSTEMS

This invention relates to fuel monitoring systems and relates more especially to such systems for use in aircraft to check before take-off the specific type of fuel taken on board by the aircraft, and to monitor the actual condition of the fuel contained in the aircraft's fuel tank(s) during flight of the aircraft.

Various aircraft fuels are available including so-called Avgas (petrol), Avtag (wide-cut petrol), Avtur (parrafin) and Avcat (boiler fuel oil) and consequently it is very important to ensure that the correct type of fuel is supplied to the aircraft concerned and not mixtures of fuels or other liquids (including water), otherwise serious engine problems could well arise during or after take-off of the aircraft. Serious engine problems might also occur during take-off and during flight if the percentage air content of the aircraft's fuel exceeds certain limits. Such problems arise particularly when the aircraft is climbing and the fuel is in an undisturbed condition. Under these conditions the ambient pressure as it falls causes the volume of air contained within the fuel to expand so that the latter becomes supersaturated with air thereby producing pumping limitations which will become manifest to the pilot who will then need to level off or reduce the altitude of the aircraft. Similar pumping limitations due to supersaturation with air may also occur if the temperatures of certain fuels increase beyond particular values.

With a view to monitoring the fuel type and the percentage air content of fuel and also for initiating corrective action in certain cases, the present invention provides in the broadest sense a fuel monitoring system comprising means for aerating, and for separating air from, fuel supplied from the fuel tank(s) of an aircraft and means for producing vaporisation of the de-aerated fuel before it is re-liquified and fed back to the fuel tank(s). The fuel monitoring system enables the percentage air content of the aircraft fuel to be determined from the volume of air separated from the fuel and the vapour pressure of the fuel, and the vapour pressure of the fuel to be determined from the means producing vaporistion of the de-aerated fuel.

In carrying out the present invention the system preferably comprises a centrifugal air separation chamber having input and output Venturi devices, the system being arranged so that fuel from the fuel tank (s) of the aircraft is pumped by suitable pumping means of the system to the input Venturi device which, due to the pressure drop therein, serves to release air from the fuel before it passes into the centrifugal air separation chamber where the air released from the fuel is separated out and exhausted from the chamber, whereas the substantially de-aerated fuel passes from the separation chamber into the output Venturi device which produces a pressure drop enabling the vapour pressure of the de-aerated fuel to be determined therefrom.

The pumping efficiency of aircraft fuel pumps fall quite dramatically under conditions of high vapour to liquid ratio (i.e. air release condition) and/or low net positive suction head (i.e. boiling condition) dependent upon the difference between ambient tank pressure and vapour pressure of fuel. As will be appreciated, these conditions producing low pumping efficiency will be dependent upon the particular type of fuel being used, the temperature of such fuels and the percentage air content of fuel or air solubility. These factors can be determined before and after take-off of the aircraft from pressure measurements made at various points in the fuel monitoring system according to the invention and at measured temperatures.

The specific type of fuel taken on board the aircraft can be determined by measuring the temperature and the vapour pressure of the de-aerated fuel at the centre of the ouput Venturi device. In order to provide a double check on the type of fuel on board so as positively to exclude the possibility of the fuel tank containing water, which has a similar vapour pressure to the fuel Avtag at certain temperatures, the precentage air content of the fuel at the measured temperature can be determined either from the pressure of air before venting from the centrifugal air separation chamber or from the aerated fuel pressure at the centre of the input Venturi device. Since the percentage air content against temperature characteristic of water is quite distinct from that of the fuel Avtag the requisite positive identification of the fuel Avtag can be accomplished.

Aircraft fuels all contain air in solution (e.g. Avtur fuel contains about 15% air under normal conditions) and consequently, when the aircraft is climbing in altitude the air content of the fuel will increase in volume so that the fuel may become supersaturated with air unless the fuel is disturbed so that air is released gradually from the fuel. Supersaturation of the fuel with air may also occur if the temperature of the fuel concerned increases beyond a certain value. Under air supersaturation conditions the fuel pump (s) supplying fuel to the aircraft engines will become inefficient. To avoid or make correction for such eventualities the percentage air content of the fuel can be monitored continuously during flight of the aircraft by measuring the pressure of the separated air before it is vented from the separation chamber referred to. If this measured air pressure at a measured temperature exceeds a level which indicates the presence of too high a percentage air content in the fuel then a warning signal may be transmitted to the pilot's control panel by the air pressure measuring arrangement so that the pilot can then take the necessary action (e.g. reduce altitude or perhaps bring supplementary fuel pumps into operation).

It may here be mentioned that the percentage air content of the fuel concerned can also be reduced during a climbing procedure, or when the fuel temperature is too high, by suitable agitation or disturbance of the fuel. For this purpose the de-aerated fuel exhausted from the output Venturi device of the fuel monitoring system may be fed back into the fuel tank in such a way as to produce sufficient agitation of the fuel to enable the fuel to have air gradually released therefrom.

By way of example one embodiment of the present invention will now be described with reference to the accompanying drawings in which.

As previously mentioned the fuel monitoring system according to the present invention is arranged firstly to check the type of fuel or other liquid contained by the aircraft fuel tank (s) before take-off.

Figure 1:
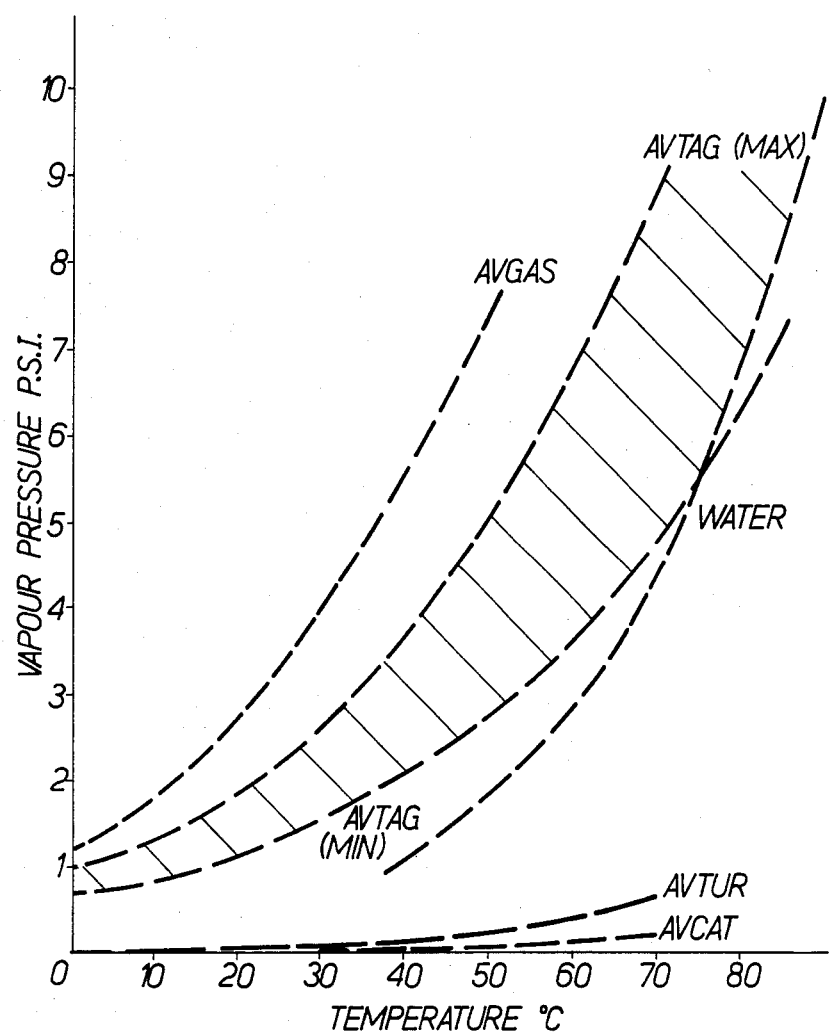
FIGS. 1, 2 and 3 show respective graphs of vapour pressures of various fuels and water against temperature, air solubility in various fuels and water against temperature and pump pressure rise against pump flow in aircraft fuel pumps.
Figure 2:
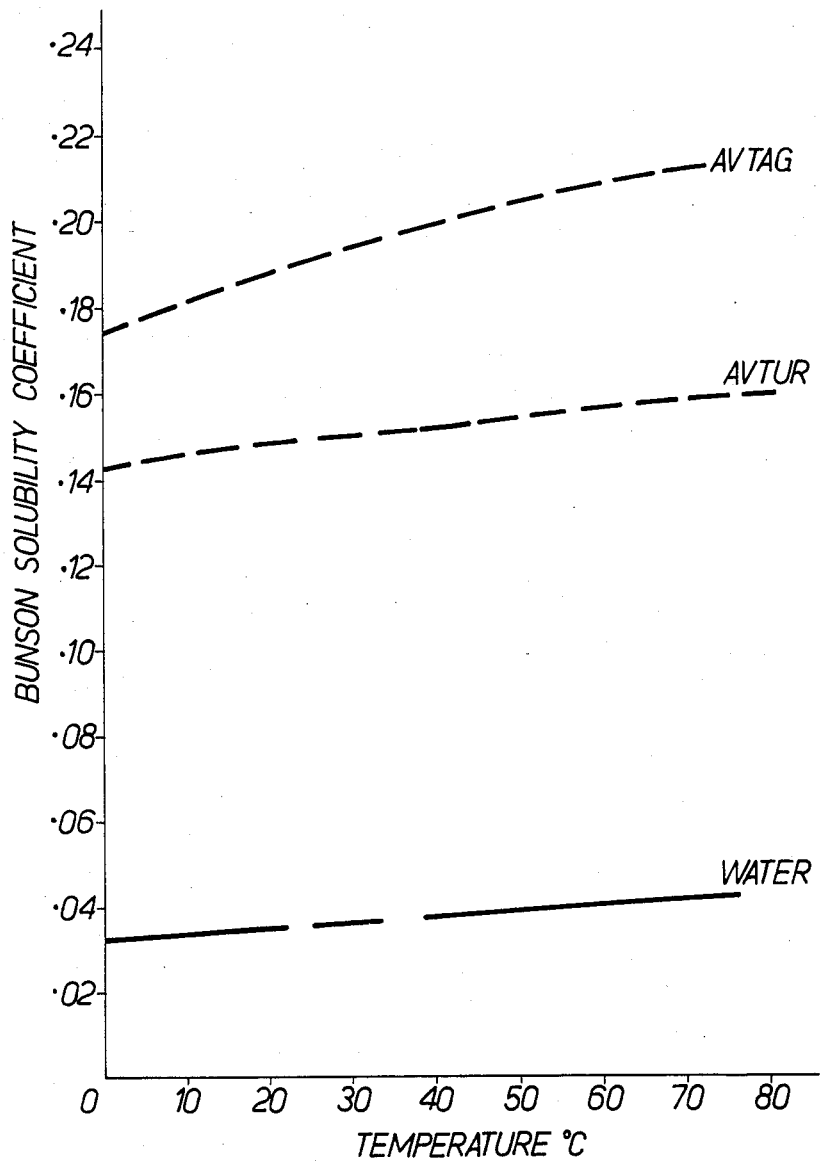

Referring to FIG. 1 of the drawings it can be seen from the graph of vapour pressure against temperature that the various aircraft fuels have readily distinguishable vapour pressure against temperature characteristics, and consequently by measuring the vapour pressure of the fuel in the tank at a measured temperature the particular fuel can be identified. However, it will also be observed that the vapour pressure against temperature characteristic for water intersects the minimum vapour pressure against temperature characteristic for the fuel Avtag at a temperature of 75° C. Consequently, at that particular temperature the liquid contained in the fuel tank could be mistakenly identified as Avtag instead of water. Thus, in order to differentiate clearly between water and Avtag the air solubility against temperature of the tank liquid can be measured. By referring to FIG. 2 which shows a graph of air solubility against temperature for aircraft fuels Avtag and Avtur, as well as water, it can be seen that the Avtag and water characteristics are well separated. Therefore, by measuring the air solubility or percentage air content of the liquid content of the fuel tank the possibility of mistaking Avtag fuel for water can be positively avoided.

Figure 4:
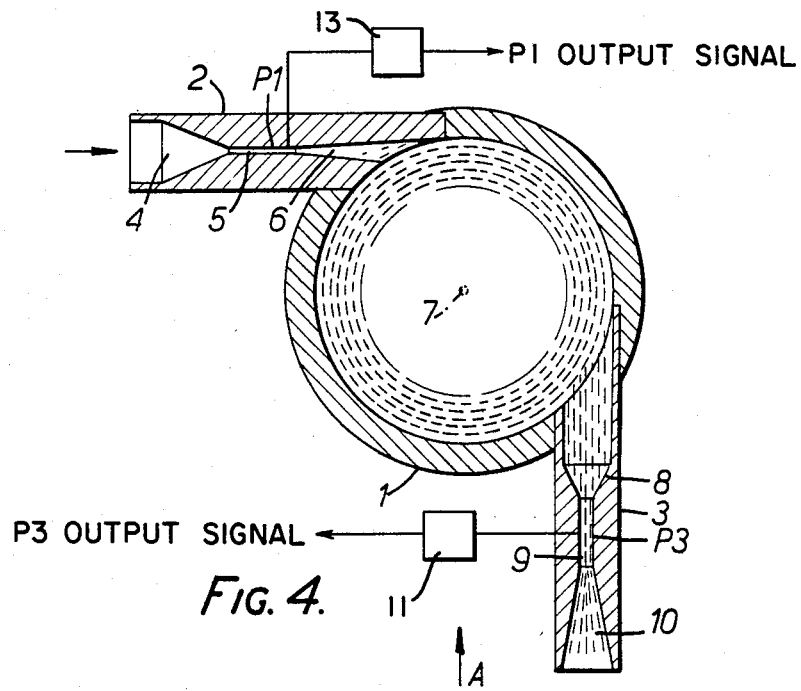
FIG. 4 is a diagrammatic cross-sectional view of fuel monitoring means comprising a centrifugal separation chamber with input and output Venturi devices.
Figure 5:
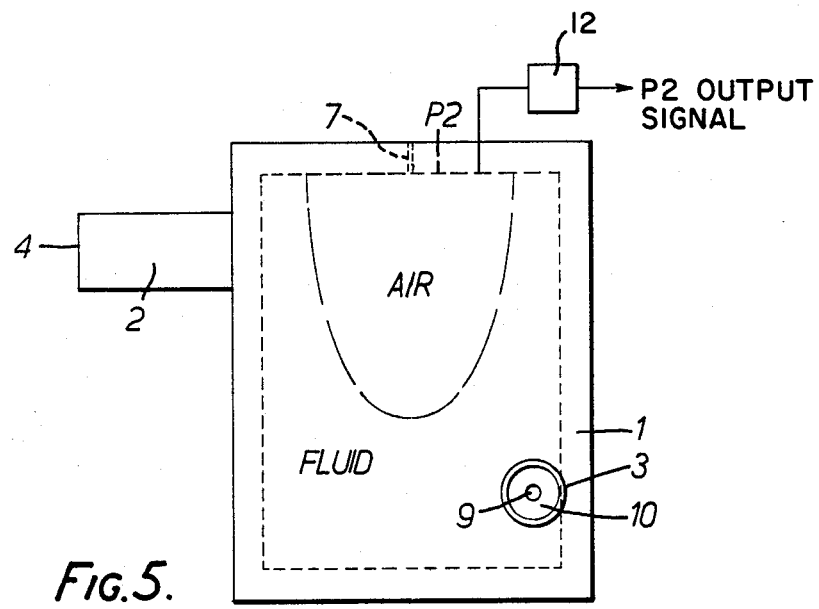
FIG. 5 shows a diagrammatic view of the fuel monitoring means of FIG. 4 taken in the direction A.

For the purpose of making these measurements to determine the fuel type the present invention provides a fuel monitoring system which, as can be seen from FIGS. 4 and 5, includes a cylindrical centrifugal air separation chamber 1 having an input Venturi device 2 and an output Venturi device 3.

The input Venturi device 2 comprises a nozzle 4 which will be connected by means of a fuel line (not shown) to a pump (not shown) for pumping fuel from the fuel tank of the aircraft to the Venturi/separation chamber structure. The incoming fuel, which will normally contain between 15% and 20% air, passes from the nozzle 4 of the Venture device 2 to the narrow throat 5. The velocity of the fuel is thereby increased and pressure of the fuel accordingly reduced (e.g. below about 14.7lbs/sq. in.) so that the air disolved in the fuel is released to aerate the fuel in the throat 5 of the Venturi device. The aerated fuel pressure at the center of input venturi device 2 is represented in FIG. 4 as P1. The pressure of the fuel is then increased very rapidly by the diffuser portion 6 of the Venturi device and, although there will inevitably be some re-absorption of the air into the fuel, the very short time factor involved keeps such re-absorption down to a minimum. The aerated fuel flows into the centrifugal air separation chamber 1 with sufficient peripheral velocity to cause the entrained air to be separated from the fuel and to be exhausted through the air vent 7. The de-aerated fuel then passes into the nozzle 8 of the output Venturi device 3 and undergoes a pressure drop to produce vaporisation of the fuel in the central throat portion 9 of the device before the pressure of the fuel is again increased by the diffuser portion 10 prior to exhausting the fuel.

The fuel exhausted from the Venturi device 3 will be fed back through a fuel line (not shown) into the aircraft fuel tank in order to produce agitation of the fuel for the purpose previously described. The air exhausted from the vent 7 may be fed back into the fuel tank.

The pressure P3 at the centre of the Venturi device 3 is the vapour pressure of the de-aerated fuel and pressure transducer means 11 may be utilised to convert this pressure into an electrical output P3 signal which can be measured to determine the vapour pressure. This measured value of vapour pressure can then be used in conjunction with the measured temperature to determine the type of fuel in the fuel tank (s) before take-off of the aircraft (see FIG. 1). In order to provide a double check on the fuel type the air presure P2 in the separation chamber, which is dependent upon the percentage air content of the fuel, may be measured by the use of pressure transducer means 12 to provide an output P2 signal and utilised in combination with the measured temperature to determine the fuel type (see FIG. 2). Signals indicating the type of fuel on board may then be transmitted to the pilot or they may be monitored by a computer control processor in the aircraft.

Figure 3:
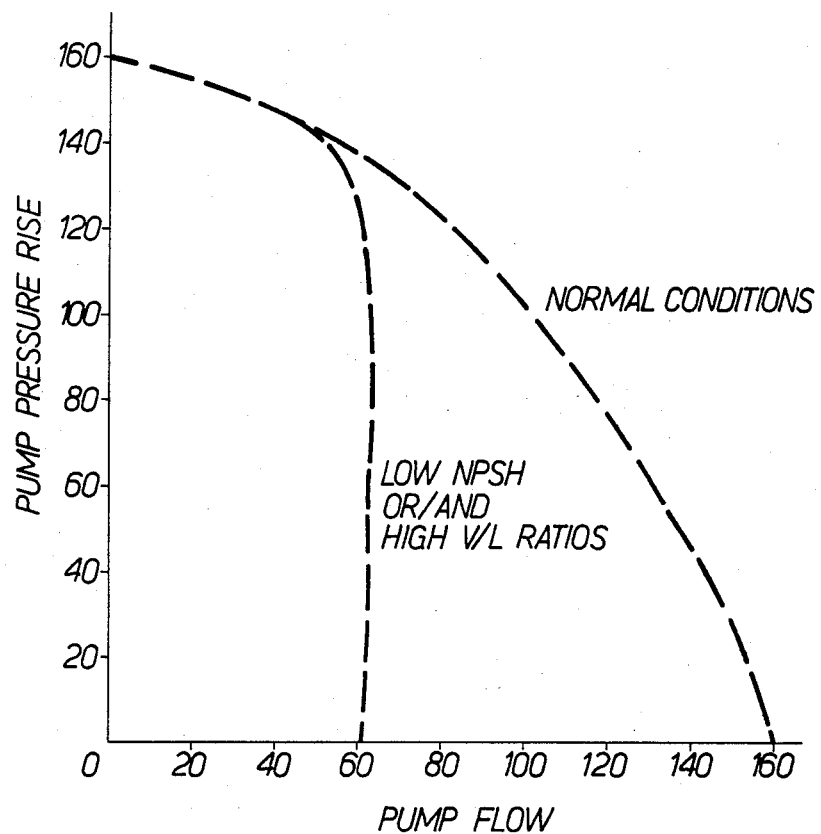

During flight of the aircraft the condition of the fuel on board may be monitored continuously to ensure that the percentage air content does not increase to a level which would present fuel pump problems as previously described. By referring to FIG. 3 of the drawings it can be seen that the fuel pump efficiency drops very sharply under conditions of high vapour to liquid ratio (air release) and/or low net positive suction head (boiling). The first of these conditions may be caused by increase in the normal percentage air content of the fuel whereas the second condition is caused by increasing fuel vapour pressure from the fuel or unduly high fuel temperatures. In order to monitor these conditions the pressure P2 may be measured to provide an indication of vapour to liquid ratio (percentage air content) whereas the vapour pressure P3 and the ambient tank pressure may be measured and utilised to derive the net positive suction head. When the measurements made indicate that pumping problems could arise warning signals may be generated for transmission to the pilot or the control processor for the initiation of some corrective action, such as the reduction in aircraft altitude or the introduction of supplementary fuel pumps.

Although in the specific embodiment a centrifugal air separation chamber with input and output Venturi devices is used, other means for monitoring the various factors (i.e. vapour pressure percentage air content) may be utilised. For example an optical or capacitance device could be employed to determine percentage air content of fuels.

I claim:

1. A fuel monitoring system for an aircraft, said system comprising:
    a cylindrical centrifugal air separtion chamber, input and output venturi devices positioned tangentially with respect to the separation chamber for tangentially conveying fuel into and out of said separation chamber, respectively, conveying means for conveying fuel from a fuel tank of an aircraft to the input venturi device which, due to the pressure drop of the fuel therein serves to release air from the fuel before it passes into the centrifugal air separation chamber where the air released from the fuel is separated out to provide substantially de-aerated fuel, air vent means for exhausting air from the separtion chamber, tangential passageway means for conducting de-aerated fuel from the separtion chamber into the output venturi device to produce a pressure drop in the de-aerated fuel, and pressure transducer means connected to the center of the output venturi device for measuring the pressure of the de-aerated fuel and for providing a pressure signal for use in determining the vapor pressure of the de-aerated fuel.

2. A fuel monitoring system as claimed in claim 1, including pressure transducer means connected to the separation chamber for measuring the pressure of air within the separation chamber and for providing a signal for use in determining the percentage air content of the fuel at a measured temperature.

3. A fuel monitoring system as claimed in claim 1, including pressure measuring means connected to the center of the input venturi device for measuring the pressure of fuel at the center of the imput venturi device for providing a signal for use in determining the percentage air content of the fuel.

* * * * *